United States Patent [19]
Leshchiner et al.

[11] Patent Number: 5,246,698
[45] Date of Patent: Sep. 21, 1993

[54] BIOCOMPATIBLE VISCOELASTIC GEL SLURRIES, THEIR PREPARATION AND USE

[75] Inventors: Edward Leshchiner, Cresskill; Endre A. Balazs, Fort Lee, both of N.J.; Nancy E. Larsen, Highland Mills, N.Y.; Adelya Leshchiner, Cresskill, N.J.

[73] Assignee: Biomatrix, Inc., Ridgefield, N.J.

[21] Appl. No.: 811,139

[22] Filed: Dec. 20, 1991

Related U.S. Application Data

[62] Division of Ser. No. 550,287, Jul. 9, 1990, Pat. No. 5,143,724.

[51] Int. Cl.$^5$ .................. A61K 31/74; A61K 37/02; A61K 31/715
[52] U.S. Cl. .................. 424/78.08; 424/78.04; 424/78.06; 424/78.14; 424/78.31; 424/428; 514/54; 514/944; 252/315; 252/315.1; 252/315.3; 530/813; 530/402; 530/411; 536/55.3
[58] Field of Search .............. 252/315.01, 315.1, 315.3; 424/78.08, 78.02–78.04, 78.06, 78.14, 426, 428, 78.24, 78.31; 516/54, 944; 530/813, 402, 411; 524/27; 536/55.1–55.3

[56] References Cited

U.S. PATENT DOCUMENTS

| | | | |
|---|---|---|---|
| 4,040,484 | 8/1977 | Hessert | 252/315.3 |
| 4,299,231 | 11/1981 | Karmann | 252/315.3 |
| 4,582,865 | 4/1986 | Balazs | 514/781 |
| 4,676,976 | 6/1987 | Toba | 252/315.3 |
| 4,702,848 | 4/1987 | Payne | 252/315.3 |
| 4,778,836 | 10/1988 | Farrer | 252/315.3 |
| 4,826,700 | 5/1989 | Bayerlein | 252/315.3 |
| 4,906,488 | 3/1990 | Pera | 252/315.3 |

Primary Examiner—Thurman K. Page
Assistant Examiner—G. S. Kishore
Attorney, Agent, or Firm—Sheldon Palmer

[57] ABSTRACT

Disclosed are biocompatible viscoelastic gel slurries formed from a polymeric gel, preferably a hyaluronan or a derivative thereof such as hylan swollen in an aqueous medium and a fluid phase which is an aqueous solution of a polymer which may also but not necessarily be a hyaluronan or derivative thereof. Also disclosed are methods of making such slurries, controlling their rheological properties and the uses thereof.

3 Claims, 7 Drawing Sheets

BIOCOMPATIBLE VISCOELASTIC GEL SLURRIES, THEIR PREPARATION AND USE

This application is a division of application Ser. No. 07/550,287, filed Jul. 9, 1990 now U.S. Pat. No. 5,143,724.

BACKGROUND OF THE INVENTION

1. Field of the Invention

The present invention relates to biocompatible viscoelastic polymeric gel slurries, methods for their preparation, formulations containing them, and medical uses thereof.

2. The Prior Art

Hereinafter, the term "polymeric gel" is used to define a system which consists of at least two components, one being solvent and the other being polymer, which is not soluble in the solvent, and which exhibits no steady-state flow. The insolubility of the polymer is provided by, or results from crosslinking which may be due to chemical bonds or crystallites or some other kind of junction (J. D. Ferry, Viscoelastic properties of polymers. John Wiley & Sons, Inc., 1961, p. 391). The solvent component usually constitutes a predominant portion of the gel. When the solvent in a gel is water, such a gel is called a hydrogel. The most widespread practical use of a hydrogel is the use of collagen gels for tissue augmentation. In such instances, a hydrogel per se is not used; rather, it is used as a viscous solution injected into the dermal or subcutaneous tissue where the collagen immediately forms a gel and forms an artificial intercellular matrix (T. R. Knapp, et al, Injectable Collagen for Soft Tissue Augmentation. Plastic and Reconstructive Surgery, Vol. 60, 1977, pp. 398–405). Another use of a hydrogel is outside the body, on the surface of the eye as contact corneal lenses (M. F. Refojo, Ophthalmic Hydrogels, in Synthetic Biomedical Polymers, Ed. M. Szycher and W. J. Robinson, Technomics, 1980, p. 171). It has also been suggested to use hydrogels for drug delivery (B. E. McCarey, et al, Current Eye Research, Vol. 3, No. 8, 1984, p. 977), for wound treatment (P. Y. Wang, Infected Skin Wounds in Rodents, Polymeric Materials and Artificial Organs. Ed. C. G. Gebelin, ACS Symposium Series 256, ACS, Washington, D.C., 1984, p. 181). The noted applications of hydrogels are based on their three major properties: (1) the ability to hold large amounts of water, (2) to create and occupy space in the intercellular matrix, and (3) to form well defined solid shapes to refract light. However, there is another property which becomes extremely important when a hydrogel is used for augmentation of the intercellular matrix as for drug delivery, namely a high level of biocompatibility which is expressed as the absence of cytotoxicity and immunogenicity and the lack of causation of inflammation and foreign body reaction.

Recently, hydrogels with exceptionally good biocompatibility have been developed. These gels are based on hyaluronan (hyaluronic acid) crosslinked with vinyl sulfone (Balazs and Leshchiner, U.S. Pat. No. 4,605,691) or on cross-linked mixtures of hyaluronan with other polymers or low molecular weight substances (Balazs and Leshchiner, U.S. Pat. No. 4,582,865). Similar gels prepared from the chemically modified hyaluronan known as hylan are also described in the prior art (Balazs, et al, U.S. Pat. No. 4,713,448). These gels are used for drug delivery (Balazs and Leshchiner, U.S. Pat. No. 4,636,524) and other purposes in the medical field (E. A. Balazs and E. A. Leshchiner (1989). Hyaluronan, its crosslinked derivative—hylan—and their medical applications, In: *Cellulosics Utilization: Research and Rewards in Cellulosics. Proceedings of the Nisshinbo International Conference on Cellulosics Utilization in the Near Future*. (Eds. Inagaki, H. and Phillips, G. O.) Elsevier, Applied Science, New York pp. 233–241.

SUMMARY OF THE INVENTION

In one aspect thereof, the present invention provides biocompatible viscoelastic gel slurries consisting of two phases; the first being a polymeric gel swollen in an aqueous medium, and the second being a fluid phase in which the said gel phase is uniformly dispersed.

In another aspect, the invention provides biocompatible viscoelastic gel slurries in which the fluid phase is an elastoviscous aqueous solution of a polymer.

In yet another aspect, the invention provides biocompatible viscoelastic gel slurries in which the gel phase comprises insoluble hyaluronan and its derivatives.

In still another aspect, the invention provides biocompatible viscoelastic gel slurries in which fluid phase comprises aqueous solutions of hyaluronan and its derivatives.

In still yet another aspect the invention provides biocompatible viscoelastic gel slurries in which the aqueous media of the gel and the fluid phase are physiologically acceptable substances, typically, water or saline.

In still yet another aspect, the invention provides viscoelastic gel slurries having varying degrees of biocompatibility specifically tailored or "engineered" to fit different medical uses.

The invention further provides methods of making these gel slurries.

Finally, the invention provides methods to control the rheological and diffusion characteristics of the instant biocompatible gel slurries.

DETAILED DESCRIPTION OF THE INVENTION

Figure 1:
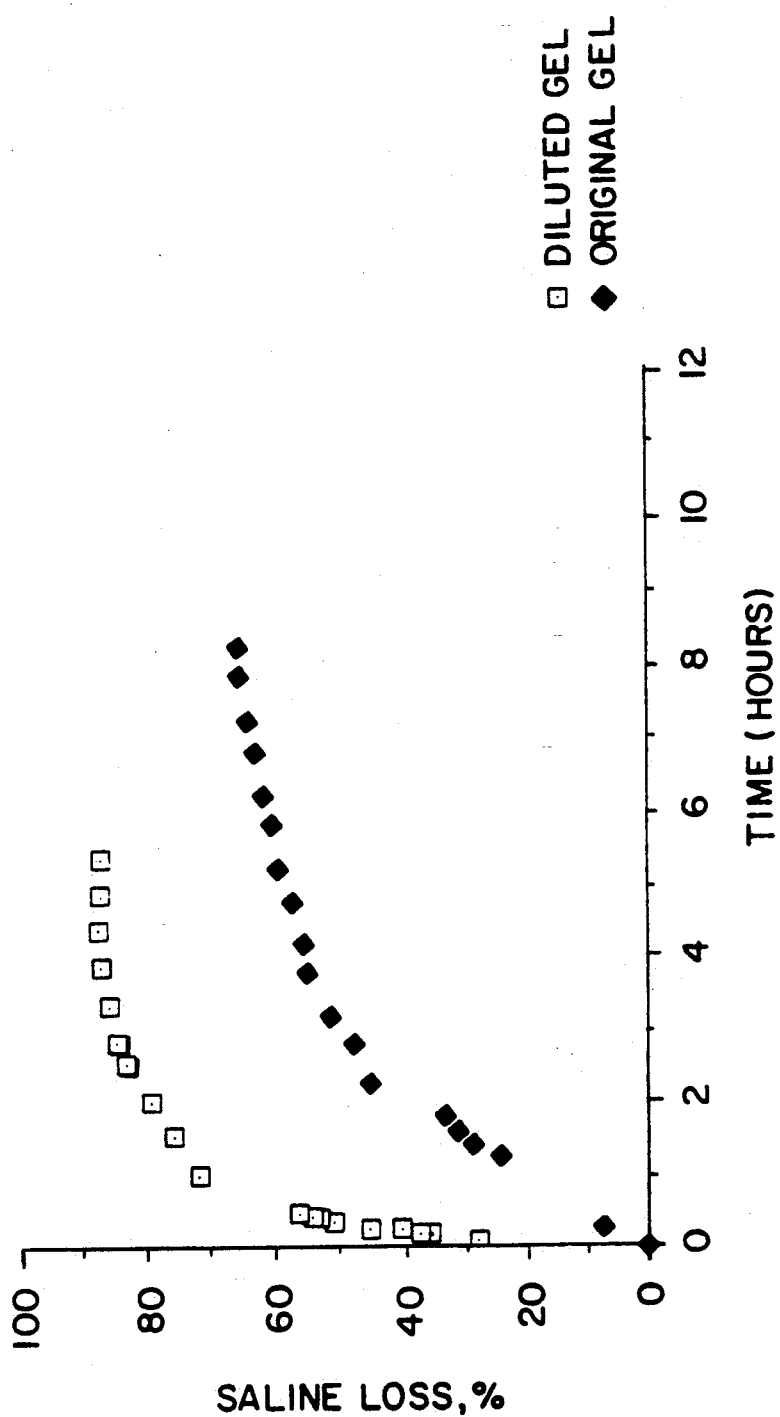
FIG. 1 is a graph showing the kinetics of compression of two viscoelastic hylan gel slurries (Example 6).

The present invention is based on the discovery that products having very unusual and extremely useful properties can be prepared in the form of two-phase gel slurries in which the first phase comprises swollen polymeric gel particles uniformly distributed in the second phase which is, preferably, a viscoelastic solution of a polymer.

There are a variety of polymeric gels suitable for the products of the present invention. The polymeric component of the gel can be a natural or a synthetic polymer. The natural polymer is selected from the group consisting of polysaccharides, proteins and nucleic acids. Examples of natural polysaccharides in this group are hyaluronan (hyaluronic acid and its biologically acceptable salts), other glycosaminoglycans, such as chondroitin sulfates, keratan sulfate, heparin, heparan sulfate, alginic acid and its biologically acceptable salts, starch, amylose, etc. Synthetic derivatives of the natural polysaccharides, such as carboxymethyl cellulose, various alkyl celluloses, hydroxyethylcellulose, carboxycellulose and oxidized starch can also be used for the purpose of the invention. Examples of suitable proteins are collagen, albumin, elastin, various globulins, etc., and their biologically acceptable synthetic derivatives.

The synthetic polymers which may be used for obtaining the gel component of the product according to the present invention include water-soluble or water-swellable polymers such as polyacrylic and polymethacrylic acids and their copolymers and derivatives such as poly(hydroxyethyl) acrylate or methacrylate, polyacrylamide, etc., polyvinyl alcohol, copolymers of maleic and fumaric acids, and the like.

Basically, there are two types of gels which may be used according to the present invention. The first one is represented by gels made of polymers which have been insolubilized by crosslinking, the crosslinks being of covalent or ionic nature. The possible crosslinking reactions are numerous and are well known to those skilled in the art. The gels of the second type are made of polymers characterized by limited affinity to specific solvents, water in the case of hydrogels, so they are not soluble in the solvent but swell in it to some degree depending on the nature of the polymer and the solvent, temperature, pH, and the presence of low molecular weight substances, etc.

In the case of crosslinked gels they can be made of mixtures of several polymers, natural or synthetic, belonging to the same or different classes of compounds. In the description of the invention these gels will be referred to as "mixed gels". Examples of mixed gels are the gels prepared from mixtures of collagen and hyaluronan, from carboxymethyl cellulose and alginic acid, etc., crosslinked with a suitable agent, e.g. vinyl sulfone.

The choice of the gel forming polymers depends on the final or intended use of the product according to the present invention and they should, in any event, possess a certain degree of biocompatibility depending on their specific application in the medical field. The term "biocompatibility" as used herein means in the most broad sense, the absence or minimal development of any adverse or undesirable reaction from the living tissues coming into contact with the product of the present invention. The possible adverse reactions include toxicity, inflammation, immune reaction, foreign-body reaction, encapsulation, etc. Depending on the specific applications, the requirements regarding the degree of biocompatibility may vary substantially.

Various gel forming polymers can provide a different degree of biocompatibility. Among the most biocompatible polymers are glycosaminoglycans and, especially, hyaluronan and its derivatives, such as hylan which is a chemically modified hyaluronan. The methods of producing hylan and crosslinked gels from hylan are described in detail in the U.S. Pat. No. 4,713,448.

Simple and mixed gels based on hyaluronan are described in U.S. Pat. Nos. 4,582,865 and No. 4,605,691. Some properties and the biocompatibility of hylan and hylan gels are described in the article by Balazs and Leshchiner (1989). Hyaluronan, its crosslinked derivative—hylan—and their medical applications, In: *Cellulosics Utilization: Research and Rewards in Cellulosics. Proceedings of the Nisshinbo International Conference on Cellulosics Utilization in the Near Future.* (Eds. Inagaki, H. and Phillips, G. O.) Elsevier, Applied Science, New York, pp. 233-241.

It should be understood that hyaluronan of any origin may be successfully used for the purpose of this invention whether it is extracted from animal tissues such as rooster combs, umbilical cord, etc., or produced microbiologically by culturing suitable bacteria. Numerous methods of producing hyaluronan are described in the prior art and are well known to those skilled in the art.

Other natural polymers like proteins, starch and cellulose derivatives have somewhat lower biocompatibility which may be expressed in noticeable immunogenicity, mild inflammatory reaction, etc. Nevertheless, gels made of these polymers may still be useful in some medical applications where a high degree of biocompatibility is not mandatory. It should be mentioned that by combining a polymer with a very high biocompatibility with another one characterized by somewhat lower biocompatibility one can increase the biocompatibility of the final gel. Hyaluronan and its derivatives are the best candidates for this purpose because of their exceptionally good biocompatibility.

The second phase in the viscoelastic gel slurries according to the present invention is usually a viscoelastic solution of one or more polymers whose rheological properties may vary over broad limits. It is clear that the gel and the solution phases should have the same solvent. In the case of a hydrogel this will be an aqueous solution of a salt or other low molecular weight substance. The choice of the polymer(s) for the fluid phase is governed by several considerations among which are the polymer biocompatibility, its compatibility with the gel phase, its metabolic pathways in vivo, the rheological properties of the polymer solutions, etc. Among the most compatible polymers suitable for the use in the products according to the present invention for the fluid phase are hyaluronan and its soluble derivatives, for example hylan, as well as other glycosaminoglycans. Examples of other water soluble polymers possessing a certain degree of biocompatibility are poly (ethylene oxides) of various molecular weights, copolymers of ethylene oxide and propylene oxide, cellulose derivatives such as carboxymethyl cellulose, hydroxypropylmethyl cellulose, hydroxyethyl cellulose, polyacrylamide, polyvinyl pyrrolidone, polyvinyl alcohol, polyacrylic acid and its copolymers, etc.

As mentioned above, the solvent component of the gel and the solution phases of the mixed gel slurries is the same and represents a physiologically acceptable aqueous medium. The latter means that the solvent itself should not cause any undesirable or adverse reaction when coming into contact with a living tissue, such as swelling or contraction of the tissue, inflammation, toxic reaction, etc. A physiologically acceptable aqueous medium is usually an aqueous solution of one or more low molecular weight substances selected from the group consisting of inorganic salts such as chlorides, sulfates, phosphates or bicarbonates of alkali or alkaline-earth metals, for example, sodium chloride, sodium sulfate, magnesium chloride, and the corresponding potassium and calcium salts; salts of organic acids such as sodium lactate, sodium glucuronate; or neutral organic substances such as glucose, mannose, polyhydric alcohols, for example, glycerol, mannitol, etc. The low molecular weight substances have a dual role, namely, providing the necessary osmotic and ionic milieu (including pH) for the final viscoelastic gel slurry. It should, however, be understood that the polymer components of the gel and the solution phases of the viscoelastic gel slurries have their own contribution to osmolarity and pH especially when these polymers are of an ionic nature. Thus, the osmolarity, pH and ion content of the solvent should be chosen with due account given to these considerations. The normal physiological range for osmolarity is 280-320 mOsm (miliosmole) and for pH is 6.8-7.2. The biocompatible viscoelastic gel slurries according to the present invention may have an osmolarity varying over broader limits depending on the specific end application. The same is true for pH especially when the solvent does not have any buffering capacity. For example, a pH of physiological saline solution which is 0.15M aqueous sodium chloride may be as low as 5.4. Thus, the osmolarity of the biocompatible viscoelastic gel slurries according to the present invention may be in the range of 50-500 mOsm, preferably, 150-400 mOsm, and a pH in the range of 5.0-8.0, preferably, 5.5-7.5, and more preferably 6.5-7.3.

In addition to biocompatibility, the other important characteristics of the gel slurries according to the present invention which determine their usefulness in various medical fields is the complex combination of their rheological properties. These properties include viscosity and its dependence on shear rate, the ratio between elastic and viscous properties in dynamic mode, relaxation behavior and some others which are discussed below in more detail. In general, the rheology of the products of the present invention can be controlled over very broad limits, essentially by two methods. According to the first such method, the rheological properties of each of the two phases forming the viscoelastic gel slurry are controlled in such a way that gives the desirable rheology for the final product. The second such method of controlling the rheology of the gel slurry consists of selecting a proper ratio for two phases. But because these parameters, i.e. rheology of the two phases and their ratio determine some other important properties of the products of the invention, the best way to control the rheology should be selected ad hoc for each specific case.

The gels suitable for the use in the products according to the present invention can represent very man different kinds of rheological bodies varying from hard fragile gels to very soft deformable fluid-like gels. Usually, for the gels which are formed without a crosslinking reaction, for example, a conventional gelatin gel, the hardness and elasticity of the gel increases with increasing polymer concentration. The rheological properties of a crosslinked gel are usually a function of several parameters such as crosslinking density, polymer concentration in the gel, composition of the solvent in which the crosslinked polymer is swollen. Gels with different rheological properties based on hyaluronan and hylan are described in the above noted U.S. Pat. Nos. 4,605,691, 4,582,865 and No. 4,713,448. According to these patents, the rheological properties of the gel can be controlled, mainly, by changing the polymer concentration in the starting reaction mixture and the ratio of the polymer and the crosslinking agent, vinyl sulfone. These two parameters determine the equilibrium swelling ratio of the resulting gel and, hence, the polymer concentration in the final product and its rheological properties.

We have now discovered another method to control the polymer concentration in the gel and its rheological properties. We have found that a substantial amount of solvent can be removed from a gel which had previously been allowed to swell to equilibrium, by mechanical compression of the gel. The compression can be achieved by applying pressure to the gel in a closed vessel with a screen which is permeable to the solvent and impermeable to the gel. The pressure can be applied to the gel directly by means of any suitable device or through a gas layer, conveniently through the air. The other way of compressing the gel is by applying centrifugal force to the gel in a vessel which has at its bottom the above mentioned semipermeable membrane. Such an apparatus suitable for gel compression is described in Example 5.

The compressibility of a polymeric gel slurry depends on many factors among which are the chemical nature of the gel, size of the gel particles, polymer concentration and the presence of a free solvent in the gel slurry. The data presented in FIG. 1 illustrate the effect of the presence of free saline in a hylan gel slurry on its compressibility. In general, when a gel slurry is subjected to pressure the removal of any free solvent present in the slurry proceeds fast and is followed by a much slower removal of the solvent from the gel particles. The kinetics of solvent removal from a gel slurry depends on such parameters as pressure, temperature, configuration of the apparatus, size of the gel particles, and starting polymer concentration in the gel. Usually, an increase in pressure, temperature, and filtering surface area and a decrease in the gel particle size and the initial polymer concentration results in an increase in the rate of solvent removal.

Partial removal of the solvent from a gel slurry makes the slurry more coherent and substantially changes the rheological properties of the slurry. The magnitude of the changes strongly depends on the degree of compression, hereinafter defined as the ratio of the initial volume of the slurry to the volume of the compressed material The achievable degree of compression, i.e. compressibility of a gel slurry, is different for different gels. For hylan gel slurries in saline, for example, it is easy to have a degree of compression of 20 and higher.

We have found that reconstitution of the compressed gel with the same solvent to the original polymer concentration produces a gel identical to the original one. This has been proven by measuring the rheological properties and by the kinetics of solvent removal from the gel by centrifuging.

It should be understood that the polymer concentration in the gel phase of the viscoelastic mixtures according to the present invention may vary over broad ranges depending on the desired properties of the mixtures which, in turn, are determined by the final use of the mixture. In general, however, the polymer concentration in the gel phase can be from 0.01 to 30%, preferably, from 0.05 to 20%. In the case of hylan and hyaluronan pure or mixed gels, the polymer concentration in the gel is preferably, in the range of 0.1 to 10%, and more preferably, from 0.15 to 5% when the swelling solvent is physiological saline solution (0.15M aqueous sodium chloride).

As mentioned above the choice of a soluble polymer or polymers for the second phase of the viscoelastic gel slurries according to the invention is governed by many considerations determined by the final use of the product. The polymer concentration in the soluble polymer phase may vary over broad limits depending on the desired properties of the final mixture and the properties of the gel phase. If the rheological properties of the viscoelastic gel slurry are of prime concern then the concentration of the soluble polymer may be chosen accordingly with due account taken of the chemical nature of the polymer, or polymers, and its molecular weight. In general, the polymer concentration in the soluble phase may be from 0.01% to 70%, preferably from 0.02 to 40%. In the case when hylan or hyaluronan are used as the soluble polymers, their concentration may be in the range of 0.01 to 10%, preferably 0.02 to 5%. In the case where other glycosaminoglycans such as chondroitin sulfate, dermatan sulfate, etc., are used as the soluble polymers, their concentration can be substantially higher because they have a much lower molecular weight.

The two phases forming the viscoelastic gel slurries according to the invention can be mixed together by any conventional means such as any type of stirrer or mixer. The mixing should be long enough in order to achieve uniform distribution of the gel phase in the polymer solution. As mentioned above, the gel phase may already be a slurry obtained by disintegrating a gel by any conventional means such as pushing it through a mesh or a plate with openings under pressure, or by stirring at high speed with any suitable stirrer. Alternatively, the viscoelastic mixed gel slurries can be prepared by mixing large pieces of gel with the polymer solution and subsequently disintegrating the mixture with formation o the viscoelastic slurry by any conventional means discussed above. When the first method of preparing a mixed gel slurry according to the invention is used, the gel slurry phase can be made of a gel swollen to equilibrium, and in this case there is no free solvent between the gel particles, or it may have some free solvent between gel particles. In the latter case this free solvent will dilute the polymer solution used as the second phase. The third type of gel slurry used as the gel phase in the mixture is a compressed gel whose properties were discussed above. When a compressed gel slurry is mixed with a polymer solution in some cases the solvent from the solution phase will go into the gel phase and cause additional swelling of the gel phase to equilibrium when the thermodynamics of the components and their mixture allows this to occur.

The composition of the viscoelastic mixed gel slurries according to the invention can vary within broad limits. The polymer solution in the mixture can constitute from 0.1 to 99.5%, preferably, from 0.5 to 99%, more preferably, from 1 to 95%, the rest being the gel phase. The choice of the proper composition of the mixture depends on the properties and composition of the two components and is governed by the desirable properties of the slurry and its final use.

The viscoelastic gel mixtures according to the invention, in addition to the two major components, namely, the polymeric gel slurry and the polymer solution, may contain many other components such as various physiologically active substances, including drugs, fillers such as microcrystalline cellulose, metallic powders, insoluble inorganic salts, dyes, surface active substances, oils, viscosity modifiers, stabilizers, etc., all depending upon the ultimate use of the products.

The viscoelastic gel slurries according to the invention represent, essentially, a continuous polymer solution matrix in which discrete viscoelastic gel particles of regular or irregular shape are uniformly distributed and behave rheologically as fluids, in other words, they exhibit certain viscosity, elasticity and plasticity. By varying the ccmpositional parameters of the slurry, namely the polymer concentration in the gel and the solution phases, and the ratio between two phases, one may conveniently control the rheological properties of the slurry such as the viscosity at a steady flow, elasticity in dynamic mode, relaxation properties, ratio between viscous and elastic behavior, etc.

The other group of properties which are strongly affected by the compositional parameters of the viscoelastic gel slurries according to the invention relates to diffusion of various substances into the slurry and from the slurry into the surrounding environment. The diffusion processes are of great importance for some specific applications of the viscoelastic gel slurries in the medical field such as prevention of adhesion formation between tissues and drug delivery as is discussed below in more detail.

It is well known that adhesion formation between tissues is one of the most common and extremely undesirable complications after almost any kind of surgery. The mechanism of adhesion formation normally involves the formation of a fibrin clot which eventually transforms into scar tissue connecting two different tissues which normally should be separated. The adhesion causes numerous undesirable symptoms such as discomfort or pain, and may in certain cases create a life threatening situation. Quite often the adhesion formation requires another operation just to eliminate the adhesions, though there is no guarantee against the adhesion formation after re-operation. One means of eliminating adhesion is to separate the tissues affected during surgery with some material which prevents diffusion of fibrinogen into the space between the tissues thus eliminating the formation of continuous fibrin clots in the space. A biocompatible viscoelastic gel slurry can be successfully used as an adhesion preventing material. However, the diffusion of low and high molecular weight substances in the case of plain gel slurries can easily occur between gel particles especially when the slurry mixes with body fluids and gel particles are separated from each other. On the other hand, when a viscoelastic mixed gel slurry according to the invention, is implanted into the body, the polymer solution phase located between gel particles continues to restrict the diffusion even after dilution with body fluids thus preventing adhesion. Moreover, this effect would be more pronounced with a increase in polymer concentration of the polymer solution phase.

The same is true when the viscoelastic mixed gel slurries according to the invention are used as drug delivery vehicles. Each of the phases of the slurry or both phases can be loaded with a drug or any other substance having physiological activity which will slowly diffuse from the viscoelastic slurry after its implantation into the body and the diffusion rate can be conveniently controlled by changing the compositional parameters of the slurries.

We have also found that both components of the viscoelastic mixed gel slurries according to the invention affect the behavior of living cells by slowing down their movement through the media and preventing their adhesion to various surfaces. The degree of manifestation of these effects depends strongly on such factors as the composition of the two components of the mixture and their ratio, the nature of the surface and its interaction with the viscoelastic gel slurry, type of the cells, etc. But in any case this property of the viscoelastic gel slurries can be used for treatment of medical disorders where regulation of cell movement and attachment are of prime importance in cases such as cancer proliferation and metastasis.

In addition to the above two applications of biocompatible viscoelastic gel slurries according to the invention other possible applications include soft tissue augmentation, use of the material as a viscosurgical tool in opthalmology, otolaryngology and other fields, wound management, in orthopedics for the treatment of osteoarthritis, etc. In all of these applications the following basic properties of the mixed gel slurries are utilized: biocompatiblity, controlled viscoelasticity and diffusion characteristics, easily controlled residence time at the site of implantation, and easy handling of the material allowing, for example its injection through a small diameter needle.

The following methods were used for characterization of the products obtained according to the invention. The concentration of hylan or hyaluronan in solution was determined by hexuronic acid assay using the automated carbazole method (E. A. Balazs, et al, Analyt. Biochem. 12, 547 558, 1965). The concentration of hylan or hyaluronan in the gel phase was determined by a modified hexuronic acid assay as described in Example 1 of U.S. Pat. No.4,582,865.

Rheological properties were evaluated with the Bohlin Rheometer System which is a computerized rheometer with controlled shear rate and which can operate in three modes: viscometry, oscillation and relaxation. The measurements of shear viscosity at low and high shear rates characterize viscous properties of the viscoelastic gel slurries and their pseudoplasticity (the ratio of viscosities at different shear rates) which is important for many applications of the products. Measurements of viscoelastic properties at various frequencies characterized the balance between elastic (storage modulus G') and viscous (loss modulus G") properties. The relaxation characteristics were evaluated as the change of the shear modulus G with time and expressed as the ratio of two modulus values at different relaxation times.

The other methods, used for characterization of the products according to the invention are described in the following examples which illustrate preferred embodiments of the invention without, however, being a limitation thereof.

Example 1

This Example illustrates the effect of the hylan gel/hylan solution ratio on the rheological properties of a viscoelastic mixed gel slurry.

The hylan fibers were prepared from rooster combs using formaldehyde as described in Example 1 of U.S. Pat. No. 4,713,448. A hylan solution in 0.15M aqueous NaCl with a concentration of 1.13% was prepared from these fibers.

A soft hylan gel was also prepared from the hylan fibers by crosslinking with vinyl sulfone according to the procedure described in Example 11 of said patent. The hylan concentration in the gel was 0.27%. The hydrating solvent in the gel was 0.15M aqueous NaCl. The gel was disintegrated by pushing it through a porcelain plate having openings of about 1 mm. The hylan solution and the gel were mixed in various ratios with a stirring rod for about 10 minutes in a manner that provides good mixing. The various mixtures were kept for about 24 hours and the rheological properties of the mixtures were measured. The results are presented in Table 1 (below). As can be seen from the table, the rheological properties of the viscoelastic gel slurries prepared from a mixture of hylan solution and hylan gel are very dependent on the composition of the slurry. Some of them like shear viscosity at higher shear rate ($4.65s^{-1}$), storage and loss moduli (G' and G") at higher frequency (5 Hz) seem to be proportional to the total polymer content in the slurry, whereas other properties (shear viscosity at lower shear rate and storage modulus G' at lower frequency 0.01 Hz) have minimum values when the concentrations of soluble and insoluble polymers in the viscoelastic slurries are approximately equal. The frequency at which storage and loss moduli (G' and G") are equal to each other characterizes the ratio between elasticity and viscosity of the material, the lower the frequency the more expressed are the elastic properties. As seen from the table, the elasticity of the viscoelastic gel slurries increases with increasing gel content in the mixture.

TABLE 1

| Rheological Properties of the Mixtures of Example 1 | | | | | | | | | | |
|---|---|---|---|---|---|---|---|---|---|---|
| Content of the Components in the mixtures, wt. % | | Polymer Content in the mixture mg/ml | | Shear Viscosity (n) at Shear Rate Pa · s | | Pseudo-plasticity n 0.015 | Dynamic Properties (Storage Modulus G', Loss Modulus G", Cross-Over Frequency w* when G' = G") | | | |
| | | | | | | | W = 0.01 Hz | | W = 5.0 Hz | |
| hylan solution | hylan gel | soluble | insoluble | $0.015 s^{-1}$ | $4.6 s^{-1}$ | n 4.6 | G', Pa | G', Pa | G", Pa | G", Pa | w*, Hz |
| — | 100 | — | 2.70 | 131 | 3.09 | 42.4 | 13.40 | 3.22 | 23.80 | 4.07 | not formed |
| 25 | 75 | 2.83 | 2.03 | 114 | 3.65 | 31.2 | 3.43 | 3.47 | 30.91 | 9.47 | 0.011 |
| 50 | 50 | 5.65 | 1.35 | 200 | 8.72 | 22.9 | 5.20 | 6.27 | 61.62 | 18.7 | 0.020 |
| 75 | 25 | 8.48 | 0.68 | 355 | 14.9 | 23.8 | 8.25 | 11.10 | 109.03 | 30.3 | 0.029 |
| 100 | — | 11.3 | — | 553 | 24.9 | 22.2 | 13.30 | 19.70 | 189.25 | 48.3 | 0.035 |

Example 2

This Example illustrates the effect of the rheological properties of the two phases and their ratios on the rheology of the resulting viscoelastic hylan mixed gel slurries.

The hylan fibers were prepared from rooster combs according to the general procedure described in U.S. Pat. No. 4,713,448. A 1.04% solution in 0.15M aqueous NaCl was prepared from the fibers with the viscosity being somewhat higher as compared to the solution used in Example 1.

A soft hylan gel was prepared from the hylan fibers according to the general procedure outlined in Example 11 of U.S. Pat. No. 4,713,448. This gel had higher polymer concentration, 0.47 wt. %, as compared to the gel used in Example 1, and as a result, different rheological properties.

The hylan solution and the hylan gel were mixed as described in Example 1 in gel/solution ratios of 1:1 and 7:3. Clear transparent mixtures with smooth textures were obtained. The rheological properties of the mixtures and the starting materials as well are presented in Table 2.

The comparison of the data of Example 1 and this Example shows that by using gel and fluid components which have higher rheology, which may be due to a higher polymer concentration or a larger molecular weight, one can achieve any desired rheology for the viscoelastic gel slurries.

As in the previous example, it is clear that the elastic properties are enhanced with an increase of the gel fraction in the slurry which in this example is illustrated not only by decreasing the cross-over frequency with an increase of the gel fraction, but also with the slower modulus relaxation, or in other words, with retention of more modulus value for the same period of time when the relaxation of modulus is measured.

stirred in until a homogeneous mixture formed. 0.56 gr of 1,2,3,4 - diepoxybutane (97%, Aldrich Chemical Co., Inc.) was added to the solution followed by 0.008 gr of sodium borohydride (Aldrich Chemical Co., Inc.) and the mixture was stirred until it became homogeneous and the tube with the reaction mixture was kept in a water bath at 50° C. for 2 hours. The gel formed which was put into 400 cc of 0.15M aqueous NaCl (physiological saline) and 1.5 cc of 1N hydrochloric acid was added to the mixture to neutralize the alkali. The gel was kept overnight in this solution, then it was removed and washed two more times with saline. About 50 gr of clear and brittle gel was obtained which then was disintegrated into a gel slurry by pushing it through a porcelain plate with openings of about 1 mm. The polymer content in the gel was determined by dialyzing small aliquots (about 1 gr) of the product against water to remove salts and subsequent freeze-drying of the gel and drying in a vacuum oven at 50° C. and a residual pressure of about 1 mm Hg until constant weight of the samples was achieved. The average found polymer concentration was 0.85%.

Two mixtures of this gel and the above mentioned hylan solution were prepared with different ratios of the

TABLE 2

Rheological Properties of the Mixtures of Example 2

| Content of the Components in the mixtures, wt. % | | Polymer Content in the Mixtures, mg/ml | | Shear Viscosity (n) at Shear Rate Pa · s | | Pseudo-plasticity | Dynamic Properties | | | Relaxation Properties | | |
|---|---|---|---|---|---|---|---|---|---|---|---|---|
| | | | | | | | Moduli at Frequency 5 Hz, Pa | | Cross-Over Frequency | | | Modulus Retention |
| hylan solution | hylan gel | soluble | insoluble | 0.015 s⁻¹ | 4.6 s⁻¹ | n 0.015 n 14.7 | Storage G' | Loss G'' | w* Hz | Modulus G at 0.06 s, Pa | Modulus G at 5.6 s, Pa | G5.6 G0.06% |
| — | 100 | — | 4.7 | 1150 | 2.86 | 402 | 104 | 19.8 | not found | 99.4 | 74.3 | 74.7 |
| 30 | 70 | 3.1 | 3.3 | 834 | 2.55 | 327 | 112 | 14.3 | 0.0005 | 111.0 | 73.7 | 66.4 |
| 50 | 50 | 5.2 | 2.35 | 852 | 4.39 | 194 | 108 | 14.9 | 0.0011 | 80.9 | 42.9 | 53.0 |
| 100 | — | 10.4 | — | 1027 | 5.71 | 180 | 180 | 22.5 | 0.004 | 146.0 | 71.8 | 49.2 |

Example 3

This Example illustrates the properties of viscoelastic gel slurries containing hylan gels cross-linked with diepoxybutane.

The hylan fibers were prepared from rooster combs according to the general procedure described in U.S. Pat. No. 4,713,448. A hylan solution in 0.15M aqueous NaCl was prepared from the fibers with concentration 0.92%. A hylan gel was prepared from these fibers by crosslinking with diepoxybutane according to the general procedure described by T. C. Laurent in the article "Cross-Linked Gels of Hyaluronic Acid", Acta Chem. Scand. 1964, v. 18, No. 1, pp. 274-275. as follows:

0.80 gr of air-dry fibers (0.56 gr moisture free weight) were mixed with 5.8 cc of distilled water and kept overnight with occasional stirring. 0.8 cc of 2N sodium hydroxide was added to the solution obtained and components and the rheological properties of the mixtures were measured. The results are presented in Table 3. The rheological data show that the nature of the gel strongly affects the dependence of some properties on the composition of the mixtures. Thus, for the mixtures of this example which are based on a gel crosslinked with diepoxybutane there is a strong synergistic effect for shear viscosity where the viscosity of a 1:1 mixture is substantially higher than the viscosities of the individual components whereas the relaxation behavior is the same as observed in the previous examples.

TABLE 3

Rheological Properties of the Mixtures of Example 3

| Content of the Components in the mixtures, wt. % | | Polymer Content in the Mixtures, mg/ml | | Shear Viscosity (n) at Shear Rate Pa · s | | Pseudo-plasticity | Dynamic Properties | | | Relaxation Properties | | |
|---|---|---|---|---|---|---|---|---|---|---|---|---|
| | | | | | | | Moduli at Frequency 5 Hz, Pa | | Cross-Over Frequency | | | Modulus Retention |
| hylan solution | hylan gel | soluble | insoluble | 0.015 s⁻¹ | 4.6 s⁻¹ | n 0.015 n 14.7 | Storage G' | Loss G'' | w* Hz | Modulus G at 0.06 s, Pa | Modulus G at 5.6 s, Pa | G5.6 G0.06% |
| 0 | 100 | — | 8.50 | 1080 | 1.08 | 1000 | 338 | 89 | n.f. | 325 | 241 | 74 |
| 30 | 70 | 2.76 | 5.95 | 1198 | 0.426 | 2812 | 192 | 62 | n.f. | 219 | 136 | 62 |
| 50 | 50 | 4.60 | 4.25 | 2265 | 4.23 | 535 | 208 | 55 | n.f. | 234 | 102 | 44 |
| 100 | — | 9.20 | — | 361 | 3.44 | 105 | 87.5 | 20 | 0.005 | 56 | 15 | 27 |

Example 4

This Example illustrates the rheological properties of some viscoelastic mixtures of hylan gel slurry with various polymer solutions.

Hylan fibers were prepared and used for preparing hylan gel by crosslinking with vinyl sulfone according to Example 2. Mixtures of the gel with the following polymer solutions were prepared: 5 wt. % solution of polyvinyl pyrrolidone (MW 360,000, Aldrich Chemical Co., Inc.) in 0.15M saline; 1 wt. % solution of Polyox ® Coagulant (MW 5,000,000, Union Carbide Corp.) in 0.15M saline; and 5 wt. solution of Polyo ® WSR-N-10 (MW 100,000, Union Carbide Corp.) in 0.15M saline. The rheological properties of the mixtures are presented in Table 4. These data clearly illustrate the effect of the nature of the soluble polymer phase on the rheological behavior of the viscoelastic gel slurries. For the three tested polymers there are the following similarities in the rheology of the mixtures: shear viscosities and loss moduli and modulus retention in relaxation measurements increase with an increase in the amount of hylan gel in the mixtures whereas cross-over frequency shifts towards lower numbers. In other words, the whole complex of viscoelastic properties dramatically increases with addition of the gel to the polymer solution. At the same time, the extent of this increase depends very much on the chemical nature of the polymer. For example, high molecular weight Polyox ® coagulant gives a synergistic effect when mixed with the hylan gel in a ratio of 3:7 which manifests itself in a large increase of storage modulus beyond the values for the pure gel or the polymer solution.

come out of the apparatus. About 20 ml of saline was collected in 44 hours and the process of gel compression was terminated at this point.

The polymer concentration in the compressed gel was found to be 0.59% which is in good agreement with the value calculated based on the solvent loss (0.61%). The rheological properties of the starting and the compressed gel are presented int he following table.

TABLE 5

| Comparative Rheological Properties of Hylan Gel After Compression | | | | | | |
|---|---|---|---|---|---|---|
| | Dynamic Properties at 5 Hz | | | Relaxation Properties | | |
| Gel ample | | | $G'$ | G at 0.06 s, 5.6 s, G5.6 | G at | |
| Concentration | $G'$, Pa | $G''$, Pa | $G''$ | Pa | Pa | G0.06% |
| Starting, 0.53% | 114 | 37.2 | 3.06 | 83.6 | 44.1 | 52.7 |
| Compressed, 0.59% | 311 | 36.7 | 8.47 | 297 | 263 | 88.5 |

Thus, even a relatively small increase in concentration achieved through partial removal of the solvent in which the gel is swollen by compressing the gel under pressure causes a substantial increase in the elastic properties of the gel.

Example 6

TABLE 4

| Rheological Properties of the Mixtures of Example 4 | | | | | | | | | | | |
|---|---|---|---|---|---|---|---|---|---|---|---|
| Content of the Components in the mixtures, wt. % | | Polymer Content in the Mixtures, mg/ml | | Shear Viscosity (n) at Shear Rate Pa·s | | Pseudo-plasticity | Dynamic Properties Moduli at Frequency 5 Hz, Pa | | Cross-Over Frequency | Relaxation Properties | | Modulus Retention |
| polymer solution | hylan gel | soluble | insoluble | 0.015 $s^{-1}$ | 4.6 $s^{-1}$ | n 0.015 n 14.7 | Storage $G'$ | Loss $G''$ | w* Hz | Modulus G at 0.06 s, Pa | Modulus G at 5.6 s, Pa | G5.6 G0.06% |
| — | 100 | — | 5.6 | 943 | 9.56 | 99 | 103 | 8.3 | n.f. | 94 | 61 | 65 |
| Mixtures with 5% PVP Solution | | | | | | | | | | | | |
| 100 | — | 50.0 | — | 4.7 | 0.08 | 59 | 0.41 | 1.44 | 0.20 | 46 | 25 | 54 |
| 50 | 50 | 25.0 | 2.8 | 81 | 0.46 | 176 | 10.8 | 9.2 | n.f. | 6.2 | 3.3 | 53 |
| 30 | 70 | 15.0 | 3.92 | 95.7 | 0.92 | 104 | 28.5 | 15.4 | n.f. | 17.8 | 10.0 | 56 |
| Mixtures with 5% Polyox WSR-N-10 Solution | | | | | | | | | | | | |
| 100 | — | 50.0 | — | 3.5 | 0.09 | 39 | 1.3 | 1.9 | 6.2 | 1.8 | 0.08 | 4.4 |
| 50 | 50 | 25.0 | 2.8 | 181 | 0.075 | 2413 | 22.0 | 6.5 | n.f. | 18.9 | 15.5 | 82 |
| 30 | 70 | 15.0 | 3.92 | 317 | 0.09 | 3522 | 42.5 | 4.0 | n.f. | 38.0 | 33.6 | 88 |
| Mixtures with 1% Polyox Coagulant Solution | | | | | | | | | | | | |
| 100 | — | 10 | — | 12.3 | 0.52 | 24 | 7.4 | 3.1 | 0.15 | 2.01 | 0.46 | 23 |
| 50 | 50 | 5 | 2.8 | 229 | 1.2 | 191 | 59.0 | 14.8 | n.f. | 46 | 15.9 | 35 |
| 30 | 70 | 3 | 3.92 | 411 | 2.0 | 205 | 877 | 209 | n.f. | 361 | 353 | 98 |

Example 5

This Example illustrates the effect of compression of the gel on the rheological properties of hylan gel.

Hylan fibers were prepared as above and used for preparing hylan gel by crosslinking with vinyl sulfone according to Example 2 above. The hylan concentration in the gel was 0.53%. A compression apparatus consisting of a cylindrical vessel equipped with upper and bottom plates, the upper one having a gas inlet and a manometer, and the bottom one having a circular opening covered from inside with a stainless steel grid over which a cellulosic filtering material (Micro-Media ® M 20, Ertel Engineering Co.) was placed, was charged with about 150 ml of the gel which constituted about one half of the apparatus volume. Nitrogen was supplied into the vessel from a tank and a pressure of 25 psi was maintained in the apparatus above the gel. Upon application of pressure a clear saline solution started to This Example illustrates the kinetics of compression of two samples of hylan gel.

Hylan fibers were prepared and used for preparing hylan gel by crosslinking with vinyl sulfone according to Example 2. The hylan concentration in the gel was 0.51%.

The gel was compressed using nitrogen gas in the apparatus described in the previous example. The kinetics of the saline removal is shown in FIG. 1. A portion of the same starting gel was diluted with saline 1:5 (the polymer concentration in the diluted gel was 0.10%) and the diluted gel was compressed in the same manner as the original gel. The kinetics of the saline removal of this gel is also shown in FIG. 1.

The data show that when a greater amount of solvent (saline in the present case) is added to the gel swollen to equilibrium, this solvent is removed very rapidly in the compression process and thereafter the rate of solvent removal becomes essentially the same as for the undiluted gel. Thus, the compression process allows one to distinguish between free solvent, or solvent existent as a separate phase between the gel phase particles and the solvent hydrating the polymer in the gel phase.

Example 7

This Example illustrates the effect of compression of a highly swollen hylan gel on its rheological properties.

Hylan fibers were prepared according to Example 1 and the former were used for preparing a hylan gel with a high degree of swelling by crosslinking with vinyl sulfone according to the following procedure:

1.29 gr of air-dry fibers were mixed with 15 ml of water and left overnight to dissolve. 2.2 ml of 2N sodium hydroxide solution was added to the hylan solution and mixture was stirred by hand for about 15 minutes until a less viscous and homogeneous solution was obtained. 0.135 ml of vinyl sulfone (Aldrich Chemical Co.) was diluted in 3.3 ml of water and added to the alkaline hylan solution, stirred in by hand for about 10 minutes and the mixture was allowed to gel for about 2 hours. The gel which formed was put into 400 ml of distilled water and left overnight to swell. The swollen gel was put into a buchner funnel filled with a filter paper and was attached to a side-arm vacuum flask. The gel in the funnel was constantly stirred by a mechanical stirrer and washed with large amounts of distilled water with suction until the wash was neutral. About 2000 ml of hylan gel was obtained which consisted of small, highly swollen discrete particles. The polymer concentration in the gel was 0.05%. The gel was compressed in the compression apparatus used in the previous examples with a degree of compression of about 3, and the hylan concentration in the compressed gel was 0.16%. The rheological properties of the two gels are compared in the following table.

TABLE 6

Comparative Rheological Properties of Hylan Gel After Compression

| Gel Sample Concentration | Dynamic Properties at 5 Hz | | | Relaxation Properties | | |
|---|---|---|---|---|---|---|
| | G', Pa | G", Pa | G'/G" | G at 0.06 s, Pa | G at 5.6 s, Pa | G5.6/G0.06% |
| Starting, 0.05% | 8.2 | 0.4 | 20.5 | 5.2 | 1.6 | 31 |
| Compressed, 0.16% | 314 | 8.9 | 35.3 | 336 | 320 | 95 |

Example 8

This example illustrates the effect of hylan gel concentration on its rheological properties.

Hylan fibers were prepared and used for obtaining hylan gel as described in Example 2. The hylan concentration in the gel was 0.50%. Several samples of the gel with different concentrations were prepared from this starting material. A sample with a concentration of 0.1% was made by diluting the starting gel with saline, the others, with higher concentrations than 0.5% were obtained by compressing with nitrogen in the apparatus described in Example 5. The rheological properties of the gels are presented in the following table.

TABLE 7

Comparative Rheological Properties of Hylan Gels with Different Concentrations

| Gel Concentration % | Dynamic Properties at 5 Hz | | | Relaxation Properties | | |
|---|---|---|---|---|---|---|
| | G', Pa | G", Pa | G'/G" | G at 0.06 s, Pa | G at 5.6 s, Pa | G5.6/G0.06% |
| 0.10 | 24 | 6 | 4.0 | 20 | 16 | 80 |
| 0.50 | 74 | 15 | 4.9 | 60 | 28 | 47 |
| 0.54 | 103 | 20 | 5.2 | 123 | 62 | 50 |
| 1.56 | 289 | 21 | 13.8 | 264 | 204 | 77 |
| 3.12 | 1730 | 301 | 5.7 | 1930 | 1340 | 69 |

The data presented in the table shows the strong dependence of the elastic properties of the hylan gels (G') on gel concentration.

Example 9

This Example illustrates the rheological properties of a hylan gel which has been reconstituted after compression.

Figure 2:
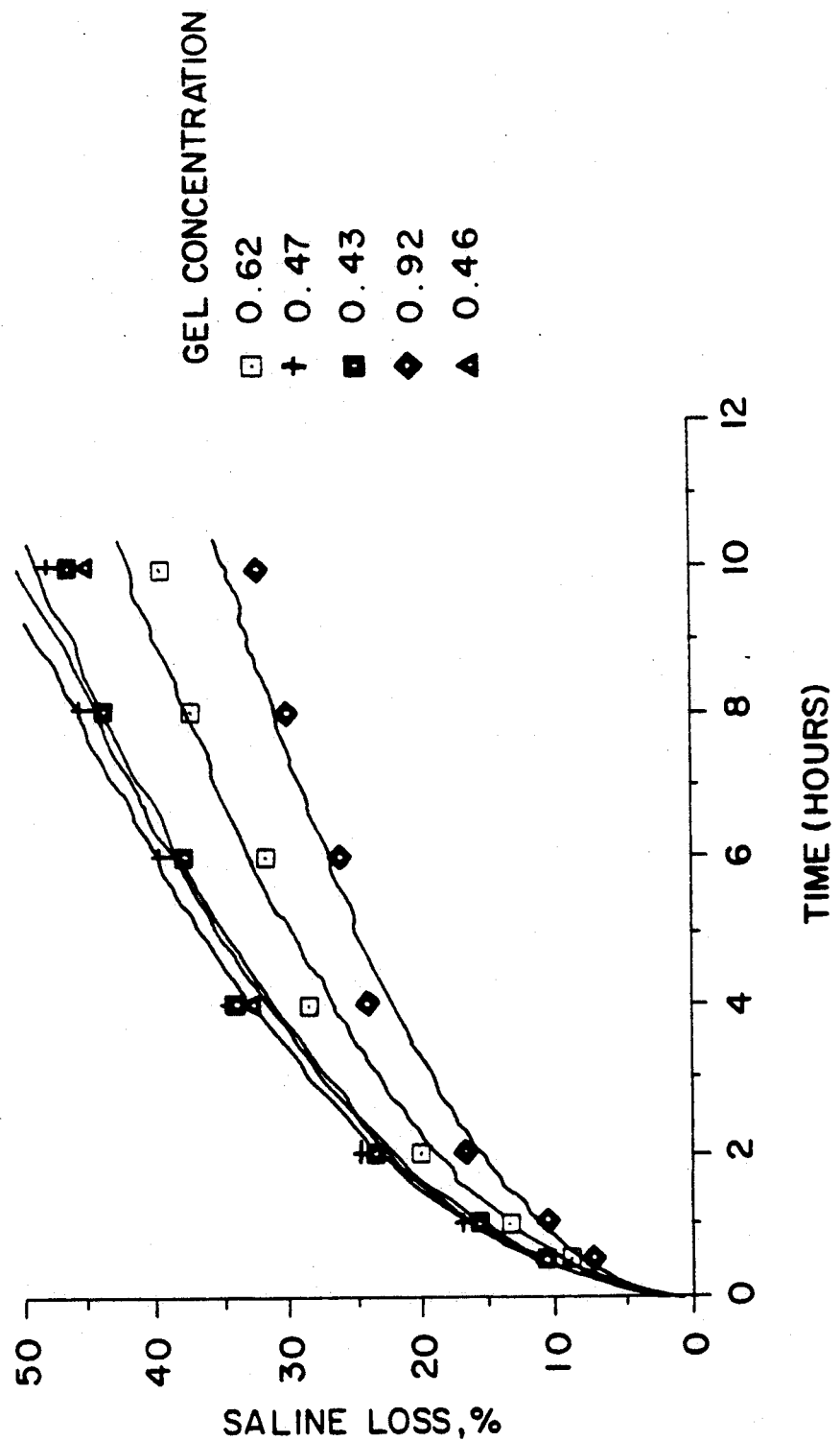
FIG. 2 is a graph showing the kinetics of solvent removal from different elastoviscous hylan gel slurries under centrifugal force (Example 9).

Hylan fibers were prepared and used for obtaining a hylan gel as described in Example 1. The hylan concentration in the gel was 0.46%. This gel was compressed as described in Example 5 for different lengths of time and two gels were produced with hylan concentrations of 0.62% and 0.92%, respectively. Both gels were reconstituted with calculated amounts of 0.15M saline and two reconstituted gel samples were obtained with hylan concentrations of 0.43% and 0.47%, respectively, which were statistically close enough to the original concentration. Rheological properties of the five gels were measured (Table 8). In addition, the kinetics of solvent removal from the gels was evaluated as follows. About two grams of a gel was put into Centricon ™ 10 microconcentrator (Amicon ®, division of Grace Co.) and spun at 2,000 rpm in a centrifuge (GLC-4, Sorvall ® Instruments, DuPont). The amounts of saline removed at predetermined time intervals were measured in % with respect to the original weight. A plot of saline loss versus time gave an exponential curve for each sample with a correlation coefficient 0.99–1.00 (FIG. 2). The kinetics of saline removal from a hylan gel sample may be described by the following equation:

$$G = B t^a,$$

where
G = saline loss %,
t = time,
B and a are constant.
The values for B and a are given in Table 8.

TABLE 8

| Sample Description | Hylan Concentration in the Gel % | Rheological Properties (Dynamic Properties at 5 Hz) | | | Constants from Equation $G = Bt^a$ | |
|---|---|---|---|---|---|---|
| | | G', Pa | G", Pa | G'/G" | B | a |
| Starting Gel | 0.46 | 70 | 12 | 5.8 | 16.1 | 0.48 |
| Reconstituted Gel I | 0.43 | 69 | 13 | 5.3 | 16.4 | 0.49 |
| Reconstituted Gel II | 0.47 | 73 | 15 | 4.9 | 16.0 | 0.49 |
| Compressed Gel I | 0.62 | 120 | 22 | 5.5 | 13.3 | 0.50 |
| Compressed | 0.92 | 145 | 27 | 5.4 | 11.0 | 0.50 |

TABLE 8-continued

| Sample Description | Hylan Concentration in the Gel %. | Rheological Properties (Dynamic Properties at 5 Hz) G', Pa | G'', Pa | G'/G'' | Constants from Equation $G = Bt^a$ B | a |
|---|---|---|---|---|---|---|
| Gel II | | | | | | |

The data presented show that reconstituted gels are essentially identical to the original equilibrated gel and are characterized by the same rheological properties and the same polymer-solvent interaction evaluated through the kinetics of solvent removal by centrifuging. The constants in the kinetic equation probably depend on the nature of the gel polymer and the solvent, parameters of centrifugation, temperature, etc., and the difference between these two constants is that the preexponential factor B depends on the gel concentration, whereas the exponent a is the same for the given gel and conditions of centrifuging.

Example 10

This Example illustrates the viscoelastic properties of some hylan mixed gel slurries.

Hylan fibers were prepared as described in Example 1. Hylan gel was obtained from hylan fibers by cross-linking with vinyl sulfone as described in Example 2. The gel was compressed as described in Example 5 to a degree of compression such that the concentration of the compressed gel was 1.5%. This gel was mixed in a ratio of 1:1 with saline and with two hylan solutions in saline which had concentrations of 2 and 5 mg/ml and which were prepared from the same hylan fibers. The rheological properties of the mixtures are presented in the following table.

TABLE 9

Comparative Rheological Properties Of Hylan Gel After Compression

| Sample No. | Sample Description | Dynamic Properties at 5 Hz G', Pa | G'', Pa | G'/G'' | Relaxation Properties G at 0.06 s, Pa | G at 5.6 s, Pa | G5.6/G0.06 % |
|---|---|---|---|---|---|---|---|
| 1 | gel-saline mixture 1:1 | 157 | 22 | 7.1 | 207 | 143 | 69 |
| 2 | gel-hylan 0.2% mixture 1:1 | 173 | 17 | 10.4 | 225 | 151 | 67 |
| 3 | gel-hylan 0.5% mixture 1:1 | 241 | 27 | 9.1 | 341 | 242 | 71 |

The data presented in the table shows that an increase in the soluble polymer concentration in the fluid phase of the gel-fluid mixture results in an increase in viscoelasticity.

Example 11

This Example illustrates the effect of adding hylan solution to a hylan gel slurry upon the injectability of the material.

Hylan fibers were prepared and used for obtaining hylan gel by crosslinking with vinyl sulfone as described in above. The hylan concentration in the gel was found to be 0.54%. The hylan fibers were also used for a 1% hylan solution in saline. Several mixtures of hylan gels with small amounts of hylan solution were prepared in the following way; a calculated amount of hylan solution was added to the gel, the mixtures were stirred with a glass rod by hand for about 10 minutes and then left for 24 hours. The procedure was repeated one more time and the samples were evaluated for ease of discharging from a syringe with a 25½ gauge needle. The following amounts of 1% hylan solution were added to the gel: 1, 2 ,4, and 10%. It was found that the addition of even a small amount of the polymer solution to the gel substantially improved the injectability of the mixture which was evaluated subjectively by a person as the degree of force which was necessary to apply to the plunger of a syringe in order to discharge the mixture at the same rate in all cases. The best injectability was observed for a mixture containing 10% of hylan solution.

Essentially the same results were obtained when solutions of hyaluronan produced microbiologically from Streptococcus Zooepidemicus (Sigma Chemical Co.) in 0.15M aqueous NaCl were used instead of hylan solutions to obtain the viscoelastic mixed gel slurries.

Example 12

This Example illustrates the effect of the chemical nature of the gels on compressibility and rheological properties.

Hylan fibers were prepared according to Example 1 and used for obtaining hylan gel and a mixed gel of hylan and carboxymethyl cellulose (CMC) by crosslinking with vinyl sulfone according to the general procedure described in Examples 1 and 10-13 of U.S. Pat. No. 4,582,865. Pure carboxymethyl cellulose gel was also prepared in a similar manner. Carboxymethyl cellulose from Hercules, 9HYF, was used. The procedure for obtaining the gels was the following: the starting material (hylan fibers, or CMC, or a 1:1 mixture of hylan and CMC) taken in an amount corresponding to 3% polymer concentration in the final reaction mixture was dissolved in water for 24 hours with occasional stirring. 1N aqueous sodium hydroxide was added to the polymer solution in such amount as to have an alkali concentration in the final mixture of 0.1N. The solution wa stirred for 30 minutes and vinyl sulfone was added to the solution in such amount to provide a weight ratio of total polymer in the final mixture to vinyl sulfone of 4.5 to 1. The vinyl sulfone was stirred in for about 10 minutes and then the reaction mixture was left for 1 hour. The gel formed (the final volume was about 50 cc) was cut into pieces and put into a large excess of saline (500 ml) and left to swell for 16 hours. The washing with saline was repeated in the same manner four more times and a highly swollen gel was transformed into a gel slurry by pushing it through a Buchner funnel under vacuum. The polymer concentration in the hylan sample was determined by the above described method, whereas for CMC and the mixed hylan-CMC gel, a weight method was used. According to this method a sample of a gel weighed to the fourth decimal point was dialyzed against distilled water with three changes of dialyzate and the retentate was freeze-dried and then dried in a vacuum oven at 50° C. for 12 hours and weighed. The polymer content was calculated as the % ratio of polymer weight to the gel weight. The gel samples were compressed with nitrogen in the apparatus described in Example 5, the nitrogen pressure being 28 psi, for 16 hours. The amount of saline removed was measured for each sample as well as rheological properties before and after compression. The data are presented in the following table (Table 10).

TABLE 10

Compressibility and Rheological Properties of Hylan and CMC Gels

| | Polymer Concentration in the gel, % | Amount of Saline removed in compression, % | Rheological Properties of Compressed Gels | | | | | |
|---|---|---|---|---|---|---|---|---|
| | | | Dynamic Properties at 5 Hz | | | Relaxation Properties | | |
| Sample description | | | G', Pa | G", Pa | G'/G" | G at 0.06 s, Pa | G at 5.6 s, Pa | G56./G0.06, % |
| CMC Gel | 0.32 | 76 | 99 | 37 | 2.7 | 61 | 31 | 51 |
| CMC-hylan 1:1 gel | 0.38 | 82 | 156 | 29 | 5.4 | 128 | 98 | 77 |
| Hylan gel | 0.49 | 40 | 185 | 32 | 5.8 | 179 | 155 | 87 |

Example 13

This Example illustrates the injectibility of a biocompatible viscoelastic mixed hylan gel slurry.

Hylan fibers were prepared according to Example 1 and used for the preparation of a 1% hylan solution in physiological saline. Hylan gel was prepared from the fibers by crosslinking with vinyl sulfone according to Example 2. The polymer concentration in the gel was 0.53%. Hylan solution and hylan gel were mixed together in a ratio of 1:4 by stirring by hand with a glass rod for 15 minutes and then the mixture was left for several days with occasional shaking. This hylan gel-solution viscoelastic slurry was compared to pure hylan gel slurry in terms cf ease of injection into intradermal tissue of guinea pigs. The site chosen for injection was selected because it provided the highest resistance. It was found that although the total polymer content was higher in the mixed gel slurry as compared to the pure gel slurry, there was an increased ease of injectability into the tissue for the mixture as compared to the pure gel. The results indicate that the hylan solution acts as a lubricant for the passage of gel particles through a small bore needle barrel and into the dense tissue.

Example 14

This Example illustrates the diffusion of proteins into viscoelastic hylan gel slurries.

Figure 3A:
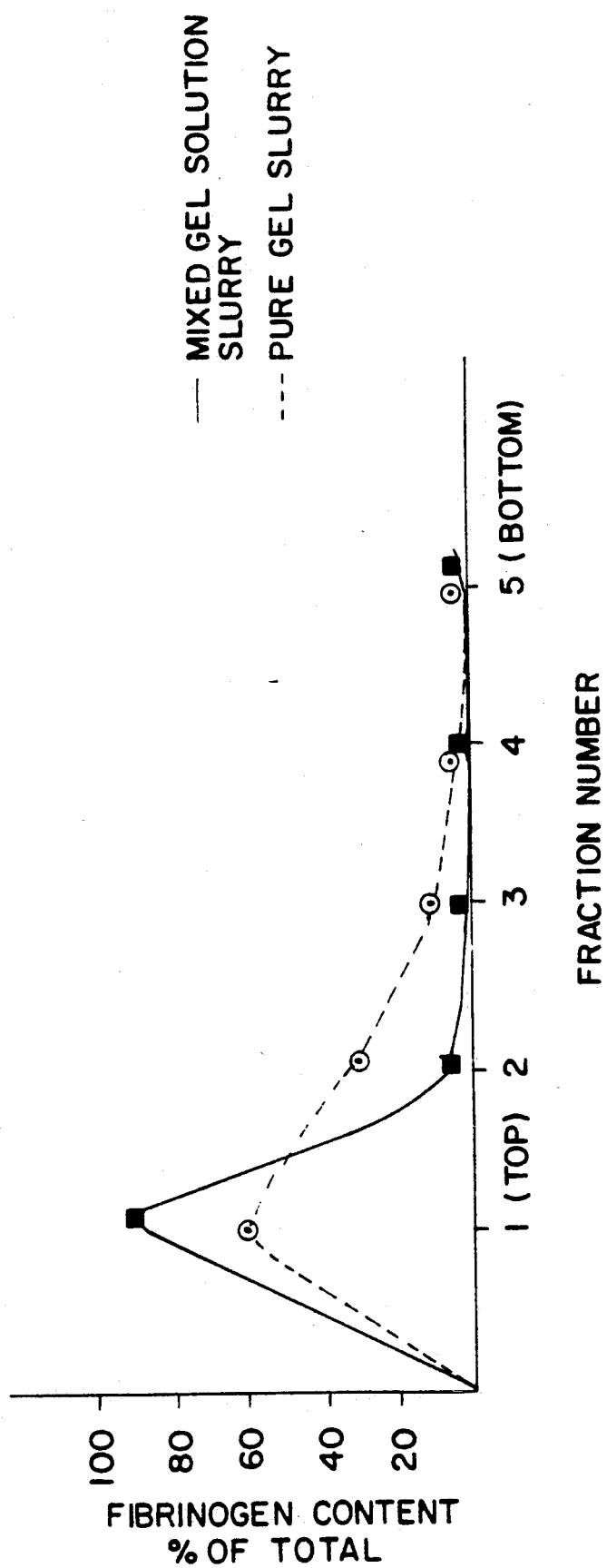
FIGS. 3a and 3b are two graphs illustrating respectively, the diffusion of fibrinogen (3a) and albumin (3b) into two different elastoviscous hylan gel slurries (Example 14).
Figure 3B:
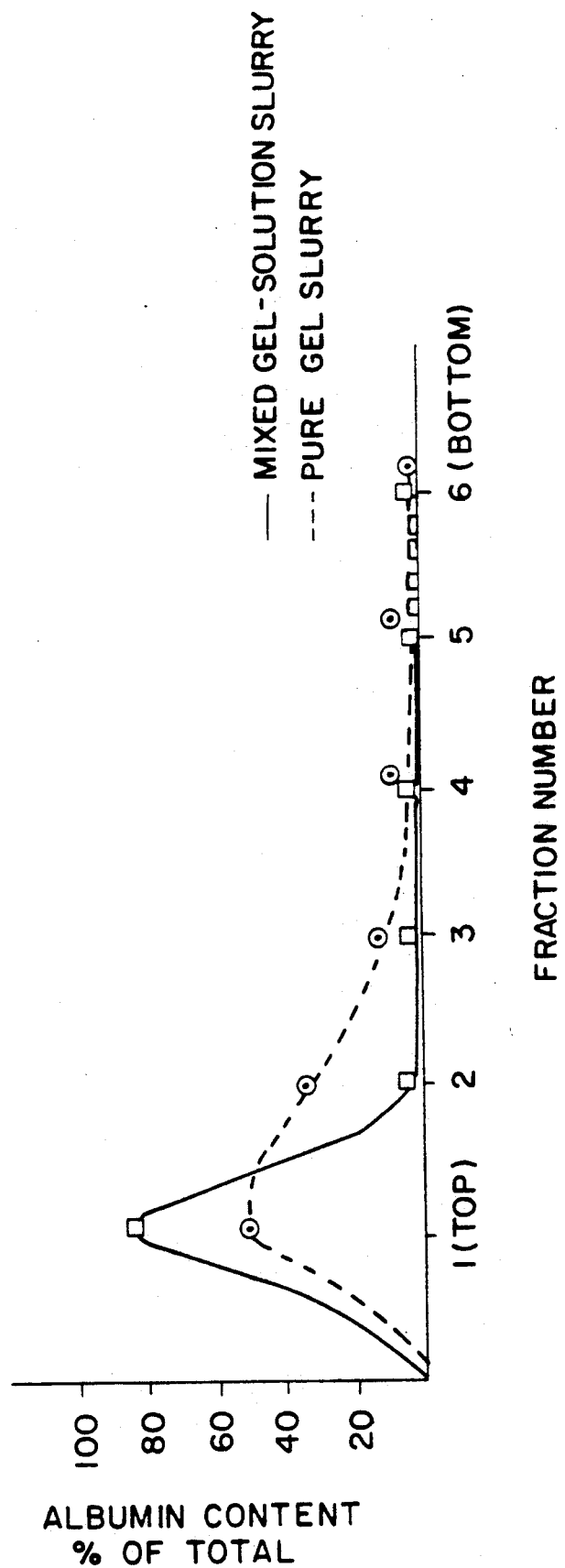

A hylan pure gel slurry and a mixed gel-solution slurry were each prepared as described in the previous example. The diffusion of two proteins, fibrinogen and albumin, through these two viscoelastic gel slurries was evaluated in the following manner. For each experiment 3 ml of a sample was loaded into a 3 ml disposable syringe. The syringe was closed at one end and was clamped in a vertical position. Radiolabeled $[^{125}I]$-fibrinogen and $[^{125}I]$-albumin obtained from New England Nuclear were used. About 0.2 ml of solution of radio-labeled protein in saline with a concentration of about 2.5 mg/ml (about $0.5 \times 10^6$ dpm for each protein sample) was applied at the top of each syringe and duplicate samples were kept at room temperature for 3 and 24 hours. After that 5 fractions, 0.5 ml volume each, were removed from each syringe and carefully transferred t test tubes for measurement of radioactivity. A Packard Auto Gamma Spectrometer was used to determine $[^{125}I]$ levels. The results are presented in the following Table 11 and in FIGS. 3 (A and B).

TABLE 11

Comparative Data for Diffusion of Fibrinogen and Albumin into Hylan Gel and Gel-Solution Mixed Slurries

| | Fibrinogen Diffusion, Content, in Fraction. % of Total | | | | Albumin Diffusion, Content Fraction, % of Total | |
|---|---|---|---|---|---|---|
| | 3 Hours | | 24 Hours | | | |
| Fraction No. | Hylan Gel | Hylan Gel-Solution Mixture | Hylan Gel | Hylan Gel-Solution Mixture | Hylan Gel | Hylan Gel-Solution Mixture |
| 1 (top) | 69.5 | 88.0 | 57.0 | 71.5 | 51.0 | 84.0 |
| 2 | 20.5 | 7.5 | 26.0 | 14.0 | 36.0 | 6.0 |
| 3 | 6.0 | 2.5 | 10.0 | 7.0 | 10.0 | 5.0 |
| 4 | 2.0 | 1.0 | 3.5 | 4.5 | 1.0 | 3.0 |
| 5 (bottom) | 3.0 | 2.0 | 4.0 | 3.0 | <1.0 | <1.0 |

The data presented show that introducing soluble hylan polymer into a mixture with the gel substantially decreases the diffusion rate of both proteins (fibrinogen and albumin) into a viscoelastic gel slurry. Int he case of the mixed gel slurry, most of the proteins stay in the top fraction, whereas in the case of pure gel slurry, this amount is substantially less. But the difference between two products becomes even more pronounced for the second fraction from the top into which from 2 to 6 times more protein penetrates int he case of pure gel slurry as compared to the gel-solution mixed slurry.

Example 15

This Example illustrates the effect of the composition of a viscoelastic material on diffusion of the fibrinogen.

The experiment of the previous example was repeated with the exception that $[^{125}I]$-fibrinogen diffusion was measured for 1% hylan solution and a 4:1 mixed slurry of hylan gel and physiological saline in addition to pure gel and mixed hylan gel-solution slurries, and the fibrinogen content was evaluated only for the two top fractions. The results are presented in the following Table 12.

TABLE 12

Comparative Data for Diffusion of $[^{125}I]$-Fibrinogen into Hylan Solution and Hylan Gel Slurries

| | Fibrinogen Content (3 Hours Diffusion), % of Total | | |
|---|---|---|---|
| Sample description | Fraction No. 1 (top), % | Fraction No. 2 % | Ratio of % fraction No. 2/ % fraction No. 1 |
| hylan gel-saline mixed slurry | 54 | 36 | 0.67 |
| hylan gel slurry | 67 | 30 | 0.45 |
| hylan solution, 1% | 70 | 27 | 0.39 |
| hylan gel-solution mixed slurry | 84 | 15 | 0.18 |

The ratio of fibrinogen content in the second and the first fraction characterizes the relative diffusion rates of fibrinogen into a sample - the less the ratio the smaller the diffusion rate. Hence, the order of relative diffusivity for the evaluated samples is gel-saline mixture > gel > hylan solution > gel-solution mixture.

Example 16

This Example illustrates the effect of the composition of a viscoelastic gel slurry on resistance to penetration of a water immicsible fluid.

The following samples were tested for moving a water immicsible dye solution through the sample under centrifugal force: hylan gel slurry and mixed hylan gel-hylan solution slurry (the same samples which were used in Example 14), mixed hylan gel-saline slurry (gel-saline ratio of 4:1), and physiological saline. 3 ml of each sample was put in a glass test tube and overlaid with 0.2 ml of 0.5% solution of Sudan Black dye in chloroform. The test tubes were centrifuged at 20 x g for 30 seconds and the distribution of the dye along the tube height was observed and recorded photographically. In the saline containing tube all of the dye solution was found at the bottom of the tube. In three other tubes the dye solution was partially collected at the bottom and partially scattered throughout the sample volume from top to bottom. The greater the amount of dye solution that was scattered through the sample and the less that was collected at the bottom, the greater was the resistance of the sample to the dye solution penetration into the sample under centrifugal force. The observed order of relative resistance for the samples was hylan gel-solution slurry > hylan gel slurry > hylan gel-saline slurry > saline.

Example 17

This Example illustrates the diffusion of a water-soluble dye into various viscoelastic hylan gel slurries.

Figure 4A:
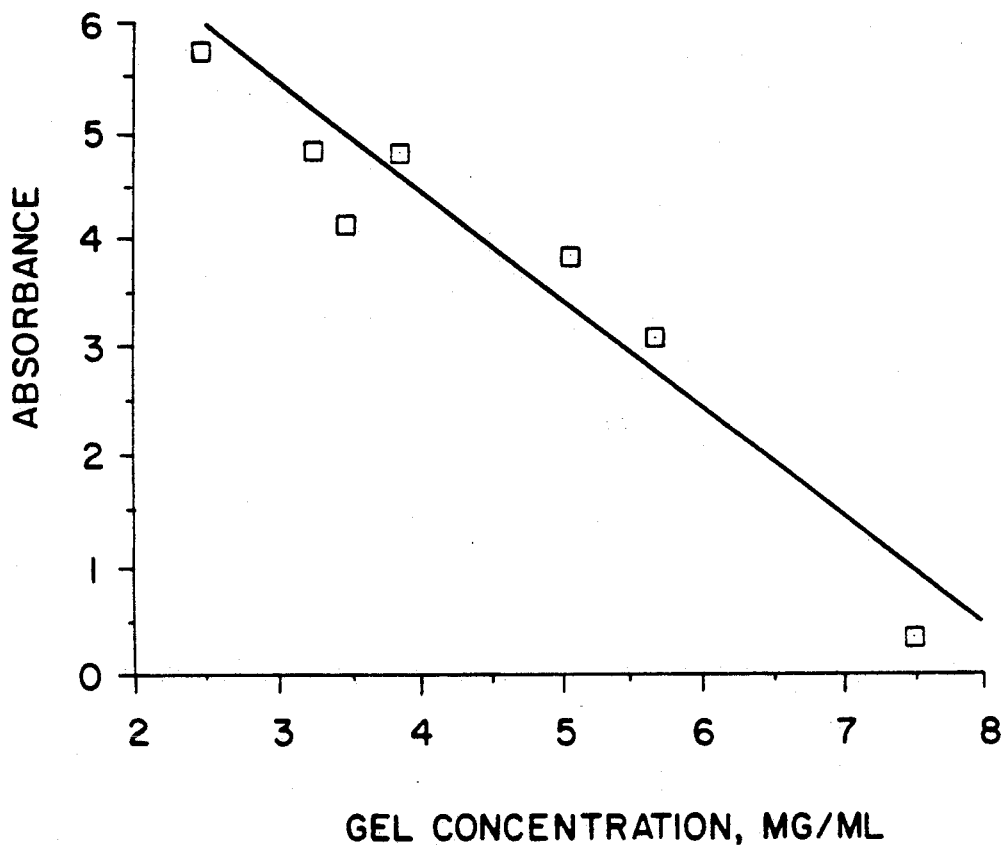
FIGS. 4a and 4b are two graphs illustrating respectively, the dependence of the amount of water-soluble dye eosin diffused into the total volume (4a) and the middle portion (4b) of various viscoelastic hylan gel slurries on their concentration (Example 17).
Figure 4B:
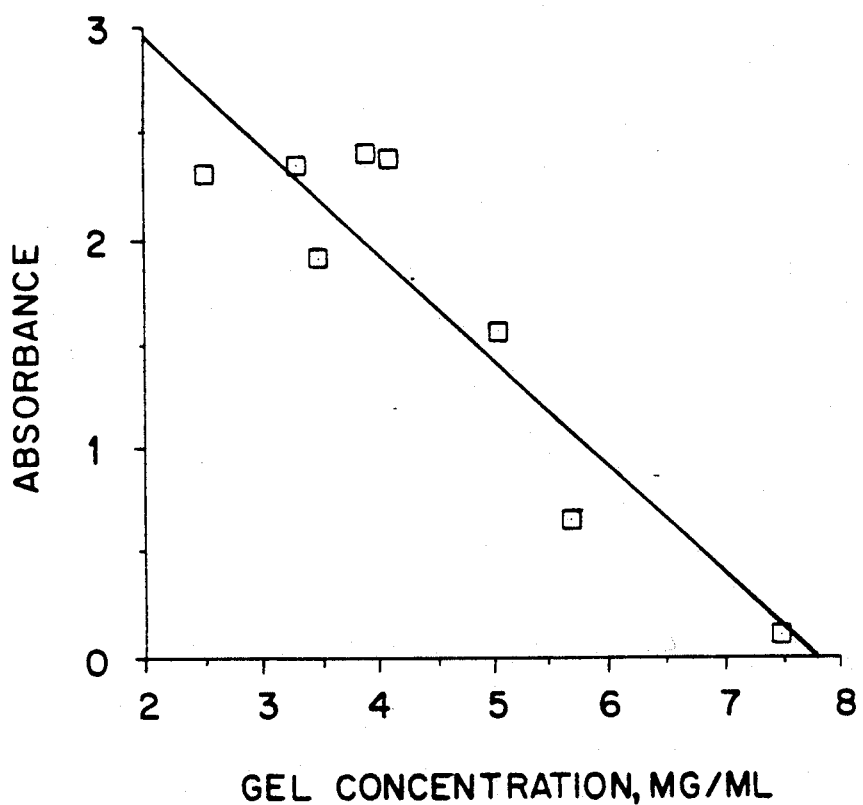

A hylan gel slurry was prepared according to Example 2. The polymer concentration in the gel was 0.53%. Four more gel slurries were prepared by diluting this gel with different amounts of physiological saline, and two more gel slurries with higher concentration by compressing the original gel slurry as described in Example 5. Thus, seven samples of hylan gel slurries were obtained with the polymer concentration ranging from 0.24 to 0.75%. The diffusion of a water-soluble dye, eosin (Aldrich Chemical Co.) into the hylan gel slurries was studied in the following way. Plastic 1 cc pipets with cut-off ends to make graduated tubes of 0.9 cc volume were filled with the gel slurries from which air bubbles were preliminarily removed by centrifuging. The bottom of each tube clamped in a vertical position was closed with a rubber stopper and an 0.1% solution of eosin in 0.15M sodium chloride was supplied to the upper end of each tube from a burette with a piece of Tygon ® tubing in such a way that there was no air gap between the gel surface and the dye solution. The head of the dye solution over the gel surface was 45 cm. The diffusion of the dye was permitted to proceed for 93 hours at room temperature (about 20° C.). Then the dye supplying tubings were disconnected and the content of each tube was separated in three equal portions of 0.3 cc each, the first (bottom), the second (middle), and the third (top). Each portion was diluted 10 times with 0.15M saline, kept overnight to equilibrate the dye concentration and the optical density at 515 nm was measured. It was found that the amount of dye diffused into the gel slurry (which wa proportional to optical density) depended linearly on the gel concentration for each of three portions and for the whole sample. The latter amount was estimated as the sum of the optical densities for the three portions. The best correlation coefficients were observed for the middle portion (0.92) and the whole sample (0.93) which may probably be explained by the suggestion that the length of the experiment enabled one to reveal the differences of diffusion rate in the best way at the height of the middle portion. The dependence of the amount of the dye penetrated into the hylan gel slurries on the polymer concentration in the gel is shown in FIGS. 4 (A and B).

Example 18

This Example illustrates the diffusion of water-soluble dye into a hylan solution and hylan gel slurries of various compositions.

To evaluate the diffusion of the water-soluble dye eosin, into a gel-polymer solution mixed slurry, the following samples were prepared. Hylan gel slurry (0.5% concentration) and a 1% hylan solution in 0.15M saline were prepared as described in Example 1. Compressed hylan gel slurries with polymer concentrations of 1.5% and 1.9% were prepared by compressing the original gel slurry according to Example 5. The compressed gel slurry with a concentration of 1.5% was mixed in a 1:1 ratio with 0.15M saline and with 0.5% hylan solution prepared from 1% hylan solution by diluting with saline. The compressed gel slurry with a concentration of 1.9% was mixed in a 1:2 ratio with 0.2% hylan solution prepared from 1% hylan solution by diluting with saline. The diffusion of 0.1% eosin solution in 0.15M saline into the hylan samples was evaluated as described in the previous example with the following exceptions. The head of the solution over the surface of the material was 50 cm. The diffusion was permitted to proceed for 18 days. The content of each pipet, 0.9 cc, was separated into 9 aliquots of 0.1 cc each. Each aliquot was mixed with 0.9 cc of distilled water, held 24 hours for dye concentration to equilibrate and the optical density was measured at 515 nm. The optical density which was proportional to the amount of the dye diffused into the sample depended exponentially on the aliquot number which was proportional to the distance of the diffusion. In other words, the diffusion of the dye into the viscoelastic hylan media (solution, gel, gel-solution mixtures) can be described by the formula:

$$m_d = B \times 10^{-ax},$$

where
$m_d$ = mass of the dye diffused,
$x$ = distance of the diffusion,
B and a - constants characterizing the sample and parameters of the diffusion (dye concentration, head of the dye solution, temperature).

Figure 5:
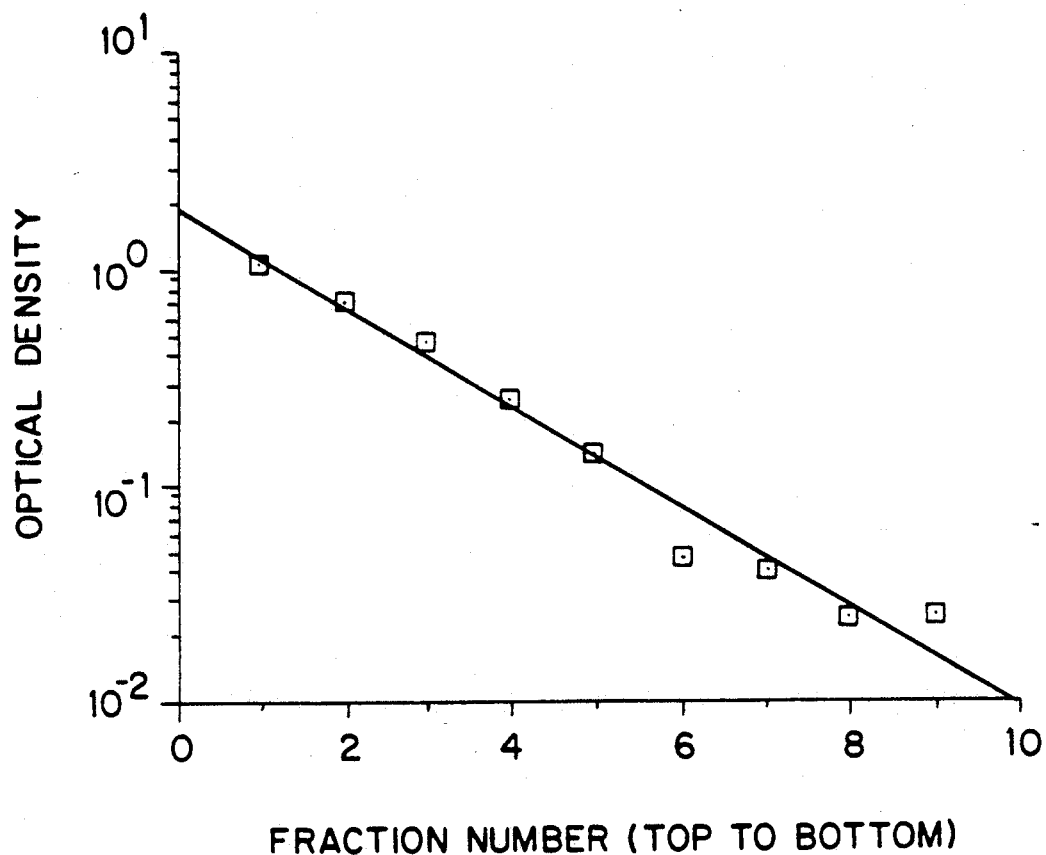
FIG. 5 is a graph showing the diffusion of eosin into a viscoelastic mixed hylan gel slurry (amount of dye diffused vs distance of diffusion (Example 18).

This dependence is represented by a straight line in semi-log coordinates with good correlation coefficients (0.98–0.99) and is shown for one of the samples in FIG. 5. The total amount of the dye penetrated into a sample was also evaluated by summation of optical densities for all aliquots. This cumulative optical density for the five tested samples is presented in the following Table 13.

TABLE 13

Diffusion of Eosin into Viscoelastic Hylan Products

| Sample No. | Description of the Sample | % Polymer Concentration | | | Cumulative OD |
|---|---|---|---|---|---|
| | | Soluble | Insoluble | Total | |
| 1 | Hylan solution | 1.0 | — | 1.0 | 3.66 |
| 2 | Hylan gel | — | 0.5 | 0.5 | 6.34 |
| 3 | Compressed gel (1.5%) mixed with saline 1:1 | — | 0.75 | 0.75 | 5.22 |
| 4 | Compressed gel (1.5%) mixed with 0.5% hylan 1:1 | 0.25 | 0.75 | 1.0 | 4.84 |
| 5 | Compressed gel (1.9%) mixed with 0.2% hylan 1:2 | 0.13 | 0.64 | 0.77 | 2.84 |

The following conclusions can be made from these data:

the diffusion rate for hylan seems to be less for 1% hylan than for a conventional gel (samples 1 and 2).

the diffusion into a gel depends on its concentration; the diffusion rate decreases with an increase in gel concentration (samples 2 and 3).

the diffusion rate into a gel-fluid mixture can be controlled by changing the ratio of soluble and insoluble components (sample 5).

Example 19

This Example illustrates the biocompatibility of a viscoelastic hylan gel mixed slurry.

A viscoelastic hylan gel mixed slurry was prepared as described in Example 1. The ratio of hylan gel slurry to hylan solution was 1:4. The biocompatibility was evaluated in vitro by Platelet Activation Test. Platelet activation (the release reaction) plays an important role in blood coagulation and when associated with medical biomaterials may have undesirable consequences such as thrombus formation, distal embolism, and occlusive thrombosis. A high level of biocompatibility is correlated with low platelet reactivity. The test was performed as follows. Platelet rich plasma (PRP) was prepared from fresh citrated human blood following venipuncture. The platelets were labeled with $[^{14}C]$-serotonin so that more than 90% of the $^{14}C$-serotonin was taken up by the platelets. For the assay, various amounts of the viscoelastic gel slurry in the range from 0.005 to 0.20 ml/ml of $[^{14}C]$-PRP were added directly to plasma in a tube. After incubation for 90 minutes at 37° C., 0.2 ml was removed from each tube, transferred to a microcentrifuge tube and centrifuged for one minute at 9000 x g. 50 µl of each supernatant was removed and $[^{14}C]$-serotonin was measured by betascintillation. Thrombin-induced $[^{14}C]$-serotonin release was used as a positive control (100% release). Percent release for all samples was determined on the basis of thrombin release. Background release (no hylan gel slurry added) was subtracted (as a baseline) from all test samples before calculation of percent release. Release of less than 10% was considered to be insignificant. The results are presented in Table 14.

TABLE 14

Biocompatibility of Viscoelastic Hylan Gel Slurry by Platelet Activation Test

| Amount of Sample Added ml/ml of $[^{14}C]$-PRP | $[^{14}C]$-Serotonin Release, % of Control, Average of 3 Samples |
|---|---|
| 0.005 | 0 + or − 0 |
| 0.013 | 0 + or − 0 |
| 0.025 | 0 + or − 0 |
| 0.050 | 0 + or − 0 |
| 0.100 | 0.82 + or − 0.05 |

Thus, the results presented in the Table show that the viscoelastic hylan gel mixed slurry according to the present invention demonstrates an extremely high level of biocompatibility in vitro.

Example 20

This Example illustrates the biocompatibility of a viscoelastic hylan gel mixed slurry.

The same viscoelastic hylan gel mixed slurry which was used in the previous Example was evaluated in vivo in the following manner. New Zealand white rabbits (male, specific pyrogen free) were anesthetized with ketamine/rompun and the knees were shaved and then cleaned with ethanol and iodine. 0.3 ml of the viscoelastic hylan gel slurry was injected intraarticularly into the knee using a 21 gauge needle. The rabbits were sacrificed one and four weeks after injection, the knees were dissected and gross observation of each knee was done. After one week the injected hylan gel mixture was present in the joint, cartilage and synovial membranes appeared normal. After four weeks no gross pathology in the synovial fluid, synovial membranes or cartilage was observed, as well. The results from control physiological buffer solution injection were similar. These findings indicate an extremely high level of biocompatibility of visoelastic hylan gel mixed slurry in vivo.

Example 21

This example illustrates the effect of viscoelastic hylan gel slurry on cell movement and attachment to the surface. Normal cartilage fibroblasts were cultured in T75 cm² flasks in the presence of $[^3H]$-thymidine (20–25 mCi per flask) until confluent. Thus labeled cells were then trypsinized, washed, and counted. Hylan gel slurries were prepared from hylan fibers by crosslinking with vinyl sulfone according to Example 2. The ratio between hylan polymer and vinyl sulfone was adjusted according to U.S. Pat. No. 4,605,691 in order to obtain gel slurries with different polymer concentrations which were found 0.17, 0.24, 0.35, and 0.47 wt. %. A 1 wt. % solution of hylan in 0.15M aqueous NaCl was also prepared. A viscoelastic mixed hylan gel slurry was prepared by mixing equal amounts of 0.35% gel with 1% hylan solution. The six samples were dialyzed against Minimal Essential Media (MEM) and used for evaluation of cell attachment in the following manner. About 0.4–0.5 ml of a sample was put into 4 wells of a 24-well R plate in such a way that the well bottom was completely covered. The same amount of MEM was used as a control. The labeled cells were suspended in MEM to concentrations from 100,000 to 1,000,000 cells/ml and 100 µl of the suspension was carefully added to the wells and the plates were incubated for 24 hours at 37° C. The content was then removed from the wells which were subsequently washed several times with 0.15M saline and the cells attached to the well surfaces were solubilized with 0.2M aqueous sodium hydroxide and the radioactivity was measured in the alkaline washes. This radioactivity was directly proportional to the number of the cells attached to the well surfaces and was used for calculating inhibition of cell attachment by the viscoelastic samples. The attachment of the cells in the control wells containing MEM was taken as 100% (no inhibition). The results are presented in Table 15.

TABLE 15

Inhibition of Cell Attachment to Solid Surfaces by Hylan Gel Slurries

| Sample Description | Polymer Concentration Weight % | Inhibition of Cell Attachment, % |
|---|---|---|
| Control | — | 0 |
| Hylan gel slurry | 0.17 | 33 |
| Hylan gel slurry | 0.24 | 62 |
| Hylan gel slurry | 0.35 | 70 |
| Hylan gel slurry | 0.47 | 87 |
| Hylan solution | 1.00 | 94 |
| Hylan gel-solution mixture 1:1 | 0.67 | 93 |

The results presented in Table 15 show that the cell movement and attachment to solid surfaces can be controlled by adjusting the polymer concentration in the hylan gel slurry and by mixing the hylan gel slurry with hylan solution with the formation of a viscoelastic hylan gel mixed slurry.

Variations and modifications can, of course, be made without departing from the spirit and scope of the invention.

Having thus described out invention what we desire to secure by Letters Patent and hereby claim is:

We claim:

1. A method of controlling the rheological and diffusion properties of a biocompatible viscoelastic gel slurry comprising a two phase mixture, a first phase being a particulate biocompatible gel phase, said gel phase comprising a chemically cross-linked glycosaminoglycan, or said glycosaminoglycan chemically co-cross-linked with at least one other polymer selected from the group consisting of polysaccharides and proteins, said gel phase being swollen in a physiologically acceptable aqueous medium and being uniformly distributed in the second phase, said second phase comprising a polymer solution of a water-soluble biocompatible polymer selected from the group consisting of polysaccharides, polyvinylpyrrolidone and polyethylenloxide in said physiologically acceptable aqueous medium, said method comprising changing the polymer concentration in the gel phase by partial removal of the physiologically acceptable aqueous medium from the equilibrated swollen gel before combining said two phases; said partial removal being effected by subjecting the gel phase to compression, such that there results a 1.05 to 1000 fold increase in the polymer concentration in the gel phase.

2. A method according to claim 1 wherein the increase in the polymer concentration is 1.1 to 500 fold.

3. A method according to claim 2 wherein the increase is 1.2 to 100 fold.

* * * * *